United States Patent [19]

Bannert

[11] Patent Number: 5,200,180
[45] Date of Patent: Apr. 6, 1993

[54] PHARMACEUTICAL COMPOSITION FOR THE TREATMENT OF THE HUMAN EYE

[76] Inventor: Christian Bannert, Miltenbergstrasse 17, D-8900 Augsburg 22, Fed. Rep. of Germany

[21] Appl. No.: 650,847

[22] Filed: Feb. 5, 1991

Related U.S. Application Data

[63] Continuation-in-part of Ser. No. 449,882, Dec. 15, 1989, abandoned.

[30] Foreign Application Priority Data

Jun. 26, 1987 [DE] Fed. Rep. of Germany ....... 3721163

[51] Int. Cl.$^5$ ................................................ A61F 2/00
[52] U.S. Cl. ..................................... 424/427; 514/912; 514/913; 514/914; 514/915; 514/944
[58] Field of Search ................. 424/427; 514/912, 913, 514/914, 915, 944

[56] References Cited

U.S. PATENT DOCUMENTS

| | | | |
|---|---|---|---|
| 3,450,814 | 6/1969 | Bechtold | 514/914 |
| 3,640,741 | 2/1972 | Etes | 106/170 |
| 3,962,414 | 6/1976 | Michaels | 424/19 |
| 4,717,713 | 1/1988 | Zatz | 514/2 |
| 4,861,760 | 8/1989 | Mazuel | 514/54 |

*Primary Examiner*—Thurman K. Page
*Assistant Examiner*—D. Gabrielle Phelan
*Attorney, Agent, or Firm*—Felfe & Lynch

[57] ABSTRACT

Two solutions capable of gel formation are simultaneously or successively applied to the mucous membrane of the eye for the purpose of treating diseases of the eye.

3 Claims, No Drawings

PHARMACEUTICAL COMPOSITION FOR THE TREATMENT OF THE HUMAN EYE

CROSS REFERENCE TO RELATED APPLICATION

This is a continuation-in-part of copending application Ser. No. 07/449,882, filed Dec. 15, 1989, now abandoned.

FIELD OF THE INVENTION

This invention relates to a pharmaceutical composition for the treatment of the human eye which is formed by combining at least two components capable of gel formation with one another.

BACKGROUND OF THE INVENTION

For the treatment of diseases of the mucous membranes, it has proved to be useful to employ gels. On the one hand, they can be used for protecting mucous membranes as well as for keeping them moist. On the other hand, they are used to apply disinfectants and other therapeutics to the mucous membrane. These gels, which are produced from synthetic or vegetable materials and may contain various active ingredients, are applied to the mucous membranes in the nasal, oral, pharyngeal and urogenital regions.

It is a disadvantage of the known gels that they adhere only poorly to the mucous membrane, so that they do not stay sufficiently long in the location where they have been applied. Consequently, a considerably greater amount of gel must be used than would itself be necessary for an effective treatment. If not too highly viscous gels are used, these pearl off from the mucous membrane and the desired action cannot be achieved.

A further problem is the application of pharmaceutical compositions to the cornea and the conjunctiva of the human eye. In eye therapy for the treatment of diseases of the eye, gels are used which are intended to act on the cornea and the conjunctiva of the eye. The residence time of these gels on the cornea and conjunctiva, which are hereinafter, for the purpose of simplicity referred to as mucous membranes, is to last as long as possible in order to keep the eye moist, on the one hand, and to allow the active ingredients to act locally, on the other hand. In the case of the previously known compositions for the treatment of the eye, it is a problem that they do not adhere sufficiently well and are washed out by the tear fluid via the tear duct. Therefore, the application must take place at shorter time intervals and with higher dosages than would be necessary if the composition adhered well, which is very unpleasant for the patient. Precisely in the case of diseases of the eye, such as the green cataract, where a continuous therapeutic treatment is necessary, it would be desirable to devise a form of application which can be used less frequently and with smaller dosages. With some other compositions the problem arises that they form a greasy film on the eye which impairs the vision. In the case of some eye diseases, for example in some cases of dry eye, a mucin deficiency develops which causes the tear fluid to wet the corneal surface insufficiently, which in turn can lead to dry spots on the cornea and to a destruction of the epithelium. Until now, no pharmaceutical composition for the improvement of this condition has been available.

OBJECTS OF THE INVENTION

It is an object of the present invention to provide a gel composition and a method for the treatment of the human eye which avoid the shortcomings of the compositions and method described in the prior art.

Another object of the present invention is to improve the adhesion of the gel composition to the mucous membrane of the eye.

Other objects and advantages of the present invention will become apparent as the description thereof proceeds.

DESCRIPTION OF THE INVENTION

The above objects are achieved by the use of at least two components capable of gel formation with one another which are applied simultaneously or successively to the mucous membrane of the eye to form in situ a pharmaceutical composition for the treatment of the eye.

Surprisingly, I have discovered that when instead of the final gel the components capable of gel formation with one another are applied to the mucous membrane and then form a gel in situ thereon, good adhesion of the gel is achieved. Gels which adhere for a long time and do not impair the ability to see are formed thereby.

Furthermore, I have found that the viscous layer formed according to the present invention is similar to the mucin film usually present on the eye. The oligosaccharide side chains of mucin carry a negative charge in the same way as the polyuronic acids of the alginates. Therefore, the gel films produced according to the present invention adhere very lastingly on the corneal surface and, moreover, stabilize the tear film which thereby adheres better and in turn wets the corneal surface better.

The two components capable of gel formation are dissolved separately from one another. The individual solutions are then applied successively or simultaneously to the eye, preferably dropwise into the lower eye lid fold.

The components of the composition according to the present invention are substances which, when mixed, lead to gel formation. They must be compatible with the mucous membrane and must not be toxic. Examples of suitable substances are combinations of alginic acid, polyguluronic acid, polymannuronic acid, propylene glycol alginic acid, polygalacturonic acid, their salts or esters or mixtures thereof.

The gel-forming components are preferably calcium salts, together with alginic acid or one of its derivatives or with a pectin with low degree of esterification. Calcium salts react with alginic acid and pectins and their derivatives, and form cross-linkages. With increasing content of the metal salt, thickening first takes place and then gel formation. Calcium salts are preferably used as metal salts, including all pharmaceutically compatible salts such as calcium chloride, or calcium salts with organic anions such as citrate, lactate, aspartate, saccharate, oxovalerate, gluconate, lactobionate and lactogluconate. Calcium gluconate is preferred.

Sodium alginate is preferred as the alginic acid derivative component, and all viscosity types thereof can be used. They are classified by the viscosity of the 1% solution, measured at 25° C. with a Brookfield viscosimeter. Commercially available alginate types are:

Very low viscous sodium alginate (5 cps),
low viscous sodium alginate (50 cps), highly viscous sodium alginate (400 cps), and
very highly viscous sodium alginate (1350 cps).

Besides alginic acid, other mono- and polysaccharides are contained in brown algae. Fucose and the ester sulfates among these are important for the mucous membrane. By suitable methods for working up brown algae, mixtures of alginates, fucose and ester sulfates can be obtained. These mixtures are also suitable as components for the gel formation in the method according to the present invention.

The two components are used in the form of solutions. The metal salt is preferably used at a concentration of 0.01 to 2.5 mMols of metal/100 ml, and the polysaccharide is preferably used at a concentration of 0.01 to 1.0 wt.-%. The particular concentration to be employed can easily be determined. It is also dependent upon the degree of viscosity of the polysaccharide which is used.

Pharmaceutically compatible liquids which readily dissolve the particular components may be used as solvents. Distilled water which contains a pharmaceutically compatible preservative is preferably used.

The gel formed according to the present invention can be used as a tear replacement liquid for the purpose of keeping the mucous membrane of the eye moist or to protect it. Furthermore, a disinfectant and/or a therapeutic agent may be added to one of the gel-forming components and can thereby be applied to the mucous membrane of the eye.

The gel obtained according to the present invention is preferably used as a carrier for a therapeutic agent. For this purpose the appropriate dose of the therapeutic agent is introduced into one of the two components solutions, and then the solutions of the two components are applied to the mucous membrane of the eye. The two solutions are preferably applied successively to the conjunctiva.

The following Examples illustrate the present invention and will enable others skilled in the art to understand it more completely. It should be understood, however, that the invention is not limited solely to the particular Examples given below.

All percentages are percentages by weight unless otherwise indicated.

EXAMPLE 1

Two solutions having the following composition were prepared:

| Solution 1: | calcium gluconate.H$_2$O | 0.1% |
| --- | --- | --- |
|  | benzalkonium chloride | 0.1% |
|  | common salt | 0.9% |
|  | distilled water | ad 100 ml |
| Solution 2: | sodium alginate | 0.1% |
|  | (very highly viscous) |  |
|  | thiomersal | 0.1% |
|  | sodium chloride | 0.9% |
|  | distilled water | ad 100 ml |

First, a drop of Solution 1 and then a drop of Solution 2 were introduced into the conjunctival sac of the eye of a human patient. A viscous liquid formed which adhered for a long time to the mucous membrane of the eye and was effective as an artificial tear liquid.

EXAMPLE 2

Eye drops were prepared for the treatment of glaucoma. For this purpose, two solutions having the following composition were prepared:

| Solution 1: | sodium alginate | 0.1% |
| --- | --- | --- |
|  | (very highly viscous) |  |
|  | isotonic borate buffer, pH 7.6 | 50 ml |
|  | sodium chloride | 0.45% |
|  | thiomersal | 0.01% |
|  | distilled water | ad 100 ml |
| Solution 2: | calcium gluconate.H$_2$O | 0.1% |
|  | sodium chloride | 0.7% |
|  | benzalkonium chloride | 0.01% |
|  | pilocarpine hydrochloride | 1% |
|  | distilled water | ad 100 ml |

For the treatment of glaucoma, first a drop of Solution 1 and then immediately thereafter a drop of Solution 2 were applied to the eye. Another possibility comprises allowing a drop of Solution 1 and a drop of Solution 2 to combine, and then immediately applying this mixture to the eye. In either case, a fine film resulted which floated on the eye and remained there for a long time.

EXAMPLE 3

The eyes of a human patient with chronic keratoconjunctivitis sicca and in with ingrowing eyelashes (trichiasis) which had to be removed regularly at certain intervals, were treated with the tear replacement liquid prepared in analogy to Example 1. The treatment was repeated three times daily. After treatment with the tear replacement liquid, a lesser irritation occurred, and the patient experienced a substantially smaller disturbing effect due to the eyelashes contacting the eyeball. Therefore, the intervals at which the eyelashes had to be pulled out because of the disturbing reaction could be increased from about one week to two weeks. These results could not be achieved with the artificial tear liquid previously used by the patient.

EXAMPLE 4

A female patient with chronic glaucoma was treated with the eye drops according to Example 2. The drops were applied at twelve hour intervals. As a result of this therapy, a normalization of the eye pressure was observed. With the previously used pilocarpine eye drops, which had to be used four to five times daily, the patient's eyes were greatly irritated, and a normalization of the eye pressure could not be achieved.

EXAMPLE 5

A patient who had suffered from blepharoconjunctivitis with sicca symptoms since 1979 and had tried numerous eye drops and eye ointments without success, was treated for four months with the eye drops according to Example 1. The frequency of application could be reduced, the subjective state of health of the patient improved, and the burning and reddening of the eyes diminished. The feeling of the presence of a foreign body in the eye also diminished.

EXAMPLE 6

A patient who for years had suffered chronically recidively from conjunctivitis sicca with burning and reddening of the eyes, especially in dry air, was treated with the eye drops according to Example 1. After two or three applications, the patient was free of complaints. Monthly checkups confirmed this diagnosis.

EXAMPLE 7

A patient with chronic conjunctivitis with marked blepharochalasis, who had suffered for years from burning and reddening of the eyes and had used various eye preparations, in some cases hourly, with only moderate success, was treated with the eye drops according to Example 1. After use of the eye drops three times daily, the condition was distinctly improved.

EXAMPLE 8

A child who, after Lyell's syndrome had run its course, suffered from severe shrinking conjunctivitis and sicca syndrome, was treated two to three times daily for a year with the eye drops according to Example 1. The drops were tolerated. Since then, the child has been substantially freer of trouble than before. Monthly checkups confirmed this diagnosis.

EXAMPLE 9

A patient who for years had suffered from chronic conjunctivitis sicca with burning and reddening of the eyes and had reacted to various other preparations with only passing improvement, was treated with the eye drops according to Example 1, which were very well tolerated. The burning of the eyes disappeared completely.

EXAMPLE 10

A patient with chronic fibrosing conjunctivitis after Lyell's syndrome had run its course was treated with the eye drops according to Example 1. The drops were very well tolerated. In comparison with other agents, the frequency of treatment could be markedly reduced. The burning of the eyes disappeared practically completely.

EXAMPLE 11

A patient with Sjögren's syndrome had for years had massive troubles, especially burning of the eyes, so that he could no longer read. He used numerous preparations without success. Treatment with the eye drops according to Example 1 led to a sudden improvement. The patient used the eye drops four to five daily. For the first time in years he could read again. A checkup after a month showed that the patient was free of trouble.

EXAMPLE 12

A patient with sicca syndrome in conjunction with Sjögren's syndrome had eye troubles for years. He used various preparations which had to be applied frequently. For three months, he was treated with the eye drops according to Example 1 which he tolerated very well. The eye troubles disappeared after using the eye drops two or three times.

EXAMPLE 13

A patient with sicca syndrome used the eye drops according to Example 1 two to three times daily. They were very well tolerated. Since then, the patient has been free of trouble.

EXAMPLE 14

A patient with chronic staphylococcal blepharokeratitis with sicca syndrome was treated for eight months with the eye drops according to Example 1. They were excellently tolerated. Over this period of eight months the patient used the drops two to three times daily with continuous and consistent success.

EXAMPLE 15

Two solutions having the following composition were prepared as starting solutions for eye drops for the treatment of glaucoma:

| Solution 1 | |
| --- | --- |
| sodium alginate (very highly viscous) | 0.1% |
| isotonic borate buffer, pH 8.5*, | 40 ml |
| sodium chloride | 0.55% |
| thiomersal | 0.01% |
| distilled water | ad 100 ml |
| Solution 2 | |
| calcium gluconate.H$_2$O | 0.1% |
| sodium chloride | 0.8% |
| benzalkonium chloride | 0.01% |

*Isotonic borate buffer was prepared according to the "borax buffer according to Palitzsch" in OPHTHALMICA, Volume 1, Pharmazeutische Grundlagen und ihre Zubereitung, Wissenschaftliche Verlagsgesellschaft mbH, Stuttgart, page 95, Table 3.2/7, (1975).

For the treatment of glaucoma, first one drop of Solution 1 and immediately thereafter a drop of Solution 2 were applied to the eye.

EXAMPLE 16

A patient with right-left closed-angle glaucoma was treated in the right eye twice daily (8 a.m./8 p.m.) with eye drops obtained according to Example 15, and in the left eye with a 0.5% solution of timolol (a known antiglaucoma agent) at the same time. The measurement of the eye pressure gave the following values:

| daily pressure measurement (hour) | base 8 a.m. | 10 a.m. | 12 noon | 2 p.m. | 4 p.m. |
| --- | --- | --- | --- | --- | --- |
| right eye (drops according to the invention 8 a.m./ 8 p.m.) | 22 | 21 | 21 | 22 | 21 |
| left eye timolol (8 a.m./8 p.m.) | 26 | 28 | 30 | 26 | 26 |

The eye drops according to the present invention gave a better action profile in comparison with the known eye drops.

EXAMPLE 17

A patient with right-left closed-angle glaucoma with identical pressure location right and left was treated in the right eye twice, at 8 a.m. and at 8 p.m., with the eye drops according to Example 15. For comparison, the left eye was treated three times, at 8 a.m., at 12 noon and at 6 p.m., with a 0.5% solution of spersacarpin and at 8 p.m. for the night with a 2% solution of pilocarpin. The values for the pressure measurement in both eyes are shown in the following Table:

| daily pressure measurement hour) | base 8 a.m. | 10 a.m. | 12 noon | 2 p.m. | 4 p.m. |
| --- | --- | --- | --- | --- | --- |
| right eye (drops according to the invention 8 a.m./ 8 p.m.) | 17 | 16 | 19 | 18 | 17 |
| left eye comparison (8 a.m./12 noon/ | 26 | 28 | 30 | 26 | 26 |

| daily pressure measurement hour) | base 8 a.m. | 10 a.m. | 12 noon | 2 p.m. | 4 p.m. |
|---|---|---|---|---|---|
| 6 p.m./8 p.m.) | | | | | |

These values show that the pressure course is practically identical with both treatments. According to the invention, the pilocarpin dosage can be reduced by a factor of 10 and, at the same time the frequency of application can be reduced. In contradistinction thereto, in the case of the use of eye drops according to the prior art, the application must be more frequent, which is unpleasant for the patient. Furthermore, the amount of pilocarpin must be higher by a factor of 10 in order to achieve the same result.

While the present invention has been illustrated with the aid of certain specific embodiments thereof, it will be readily apparent to others skilled in the art that the invention is not limited to these particular embodiments and that various changes and modifications may be made without departing from the spirit of the invention or the scope of the appended claims.

I claim:

1. The method of treating diseases of the human eye, which comprises simultaneously or successively applying to the eye at least two compounds capable of gel formation with each other, wherein the compounds capable of gel formation are a solution of a calcium salt with a concentration of 0.01 to 2.5 mmols per 100 ml and a solution of a polysaccharide with a concentration of 0.01 to 1% by weight.

2. The method of claim 1, wherein said polysaccharide is sodium alginate.

3. The method of claim 1, wherein one or both of said solutions additionally contain disinfectants, therapeutic agents, or both.

* * * * *